United States Patent [19]

Williams et al.

[11] Patent Number: 4,728,738
[45] Date of Patent: Mar. 1, 1988

[54] SMOKING COMPOSITIONS CONTAINING ACYLPYRAZINE ETHER FLAVORANTS

[75] Inventors: David L. Williams; Everett W. Southwick; Yoram Houminer, all of Richmond, Va.

[73] Assignee: Philip Morris Incorporated, New York, N.Y.

[21] Appl. No.: 782,545

[22] Filed: Oct. 1, 1985

[51] Int. Cl.$^4$ ............... C07D 241/16; C07D 241/18; C07D 405/12
[52] U.S. Cl. ................................ 544/405; 544/406
[58] Field of Search ............................. 544/406, 405

[56] References Cited

U.S. PATENT DOCUMENTS

| | | | |
|---|---|---|---|
| 3,402,051 | 9/1968 | Roberts | 99/140 |
| 3,767,428 | 10/1973 | Mookherjee et al. | 426/65 |
| 3,881,025 | 4/1975 | Flament | 426/537 |
| 3,914,227 | 10/1975 | Pittet et al. | 260/250 B |
| 3,917,872 | 11/1975 | Winter et al. | 426/537 |
| 4,002,750 | 1/1977 | Ambrosi et al. | 544/406 X |
| 4,588,813 | 5/1986 | Houminer et al. | 544/406 |

OTHER PUBLICATIONS

Tobacco International, Apr. 9, 1979, pp. 40–52, Casing Materials—Cocoa (Part I), by G. C. Harllee and J. C. Leffingwell.

J. Agric. Food Chem., vol. 25, No. 2, 1977, Smoke Compositions, An Extensive Inventigation of the Water-Soluble Portion of Cigarette Smoke by Joseph N. Schumacher et al.

Primary Examiner—Donald G. Daus
Assistant Examiner—William A. Teoli, Jr.

[57] ABSTRACT

In one of its embodiments the present invention provides a smoking composition which contains a novel type of acylpyrazine ether flavorant additive as exemplified by 1-(3-methoxy-2-pyrazinyl)-2-methyl-1-propanone.

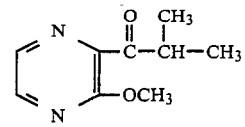

11 Claims, No Drawings

SMOKING COMPOSITIONS CONTAINING ACYLPYRAZINE ETHER FLAVORANTS

BACKGROUND OF THE INVENTION

Alkylpyrazines are typical of organic compounds which have been recognized as having useful properties for application as flavorants in tobacco and foodstuffs. Various species have been identified in natural products as flavorant or fragrance constituents.

Unlike alkylpyrazines which are ubiquitous in nature and heat-treated foodstuffs, acylpyrazines are more limited in their occurrence For example, 2-acetyl-5-methylpyrazine and 2-acetyl-5-ethylpyrazine are reported as constituents of cocoa in Tobacco International, page 18ff (March 1979), and 1-(2-pyrazinyl)-1-butanone is tentatively identified as a water-soluble component of cigarette smoke in J. Agric. Food Chem., 25(2), 310 (1977).

Several acetylpyrazines are included in the F.E.M.A. listing of food additives as being useful for imparting a popcorn-nutty flavor to a foodstuff. The incorporation of acetylpyrazine, 2-acetyl-5-methylpyrazine or 2-acetyl-6-methylpyrazine as a popcorn-like flavorant in foodstuffs and tobacco is described in U.S. Pat. No. 3,402,051.

Interest in pyrazines as flavorants or fragrances has stimulated the investigation of various types of substituted pyrazines which potentially have unique organoleptic properties.

Pyrazine flavorants characterized by the presence of an ether substituent are disclosed in U.S. Pat. Nos. 3,622,346; 3,702,253; 3,767,425; and 4,105,661.

Methoxy-substituted acetylpyrazines are reported in J. Agric. Food Chem., 23, 638(1975).

U.S. Pat. No. 4,064,124 describes a process for the manufacture of a broad variety of pyrazine derivatives via the reaction of nitrooxiranes with ammonia.

There is continuing research effort to develop new species of pyrazine type heterocyclic compounds which exhibit useful flavorant or fragrance properties.

Accordingly, it is an object of this invention to provide a novel class of acylpyrazine ether compounds which exhibit unique properties for application as flavorants. It is another object of this invention to provide a process for producing novel acylpyrazine ether compounds.

It is a further object of this invention to provide smoking compositions of tobacco and non-tobacco materials containing an acylpyrazine ether flavorant additive, which smoking compositions are adapted to impart flavor and aroma to mainstream and sidestream smoke under smoking conditions.

Other objects and advantages of the present invention shall become apparent from the accompanying description and examples.

DESCRIPTION OF THE INVENTION

One or more objects of the present invention are accomplished by the provision of a smoking composition comprising an admixture of (1) combustible filler selected from natural tobacco, reconstituted tobacco, non-tobacco substitutes, and mixtures thereof, and (2) between about 0.00001 and 2 weight percent, based on the total weight of filler, of an acylpyrazine ether corresponding to the formula:

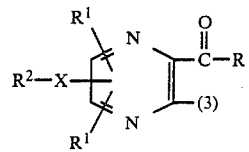

where R is a substituent selected from aliphatic, alicyclic and aromatic groups containing between about 2-12 carbon atoms, $R^1$ is a substituent selected from hydrogen and alkyl groups containing between about 1-6 carbon atoms, X is etheric oxygen or sulfur, and $R^2$ is a substituent selected from aliphatic, alicyclic and aromatic groups containing between about 1-12 carbon atoms, with the proviso that the position-(3) substituent is not hydrogen.

Illustrative of the R substituent in the represented acylpyrazine ether formula are groups which include ethyl, propyl, propanyl, butyl, pentyl, hexyl, methoxyethyl, ethoxyethyl, cyclopropyl, cyclobutyl, cyclopentyl, cyclohexyl, menthyl, furyl, tetrahydrofuryl, phenyl, tolyl, xylyl, benzyl, phenylethyl, methoxyphenyl, pyridyl, pyrazyl, and the like.

Illustrative of the $R^1$ substituents in the represented acylpyrazine ether formula are groups which include methyl, ethyl, butyl, isobutyl, pentyl, hexyl, and the like.

Illustrative of the $R^2$ substituents in the represented acylpyrazine ether formula are groups which include methyl, propyl, butenyl, butynyl, heptyl, ethoxyethyl, cyclopentyl, cyclohexenyl, furfuryl, menthyl, phenyl, benzyl, naphthyl, pyridyl, pyrazyl, and the like.

PREPARATION OF ACYLPYRAZINE ETHERS

Various specific methods of synthesizing acylpyrazine derivatives are disclosed in patents such as U.S. Pat. Nos. 3,711,482; 3,767,428; 3,890,320; and 3,914,227; and the like.

In J. Chem. Soc., Perkin II, 2035 (1972) there is reported the acylation of protonated pyrazine derivatives. In general procedure, a heteroaromatic compound (e.g., pyrazine) is acylated by reacting the compound with alkanal in the presence of t-butyl hydroperoxide and iron(II) sulfate in a homogeneous aqueous medium of acetic acid and sulfuric acid. Related procedures are disclosed in J. Chem. Soc.(C), 229(1970).

In another embodiment, the present invention provides an efficient method for the preparation of novel acylpyrazine ethers which involves the steps of (1) providing a heterogeneous reaction medium consisting of a water-immiscible organic phase and an acidic aqueous phase, wherein the organic phase comprises a mixture of a R—CHO aldehyde compound and a halopyrazine compound corresponding to the formula:

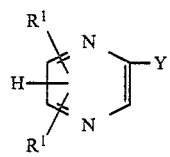

where Y is a halogen atom, and $R^1$ is a substituent selected from hydrogen and alkyl groups containing between about 1-6 carbon atoms, and R in the aldehyde compound is a substituent selected from aliphatic, alicyclic and aromatic groups containing between about 2-12 carbon atoms; (2) maintaining efficient contact between the organic and aqueous phases for a period of time sufficient to achieve acylation of the halopyrazine compound in the presence of a free radical generating agent; (3) recovering a halo-acylpyrazine intermediate corresponding to the formula:

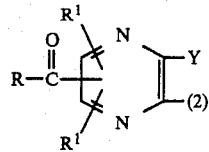

where Y is a halogen atom, R is a substituent selected from aliphatic, alicyclic and aromatic groups containing between about 2-12 carbon atoms, and $R^1$ is a substituent selected from hydrogen and alkyl groups containing between about 1-6 carbon atoms, with the proviso that the position-(2) substituent is not hydrogen; and (4) reacting the haloacylpyrazine intermediate with a $R^2$—X—M alcoholate, where M is an alkali metal atom (e.g., sodium, potassium or lithium), in a liquid medium under conditions that yield an acylpyrazine ether corresponding to the formula:

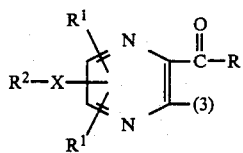

where R is a substituent selected from aliphatic, alicyclic and aromatic groups containing between about 2-12 carbon atoms, $R^1$ is a substituent selected from hydrogen and alkyl groups containing between about 1-6 carbon atoms, X is etheric oxygen or sulfur, and $R^2$ is a substituent selected from aliphatic, alicyclic and aromatic groups containing between about 1-12 carbon atoms, with the proviso that the position-(3) substituent is not hydrogen.

R, $R^1$ and $R^2$ are substituents of the type previously illustrated hereinabove. Y is a halogen atom such as chlorine, bromine or iodine.

The aldehyde (R—CHO) reactant in step (1) can be any compound which does not contain a substituent which inhibits or prevents the free radical interaction of the aldehyde functionality with the pyrazine nucleus. It is preferred that the aldehyde reactant is at least partially soluble in the aqueous phase of the acylation system, in order to increase the rate and efficiency of the acylation reaction.

The halopyrazine and aldehyde reactants can be employed over a wide range of molar ratios. It has been found convenient and advantageous to employ a molar ratio between about 0.5-10:1 of aldehyde to halopyrazine in the acylation system.

The relative volumes of the respective immiscible phases in the acylation system are not critical, and typically the two phases will be approximately equal in volume.

The acidity of the aqueous phase is provided by the addition of a suitable acid reagent such as sulfuric acid, hydrochloric acid, phosphoric acid, and the like. The pH of the aqueous phase is below about 6, and preferably is in the range between about 1-5.

The organic phase usually will comprise a mixture of the pyrazine and aldehyde reactants. If the water-solubility of the halopyrazine and aldehyde reactants are at a sufficiently high level to prevent the maintenance of separate organic and aqueous phases, then suitable modification of the acylation system is required to accomplish the separation of phases. Cooling of the acylation system is one means of providing the desired phase separation, particularly in combination with other means such as salting of the aqueous phase. A preferred alternative is to include a water-immiscible solvent in the system, such as hexane, benzene or toluene, since it provides additional advantages such as higher product yield and more efficient product recovery.

The acylation reaction between the halopyrazine and aldehyde reactants is catalyzed by the inclusion of a free radical generating agent, in a quantity between about 1-50 weight percent, based on the weight of aldehyde reactant.

Illustrative of suitable free radical initiators are hydrogen peroxide; alkali metal or ammonium persulfates, perborates, peracetates and percarbonates; organic peroxides and hydroperoxides such as benzoyl peroxide, t-butyl hydroperoxide and diisopropylperoxydicarbonate; and the like. The initiator may be associated with activating means (e.g., a redox system) which involves the use of compounds such as sulfites and thiosulfites, and redox reaction promoters such as transition metal ions (e.g., $Fe^{++}$).

The step (4) nucleophilic reaction, which introduces an etheric substituent in place of a halogen substituent in the pyrazine ring, proceeds readily in a solvent medium (e.g., ethanol) at 0°–60° C. employing approximately equimolar proportions of halo-acylpyrazine and alcoholate reactants. The acylpyrazine ether product can be recovered by conventional means such as extraction with an organic solvent.

The halo-acylpyrazine intermediate recovered in step (3) of the process is a novel type of pyrazine derivative. Thus, in a further embodiment the present invention provides a class of halo-acylpyrazines which can be prepared by a process which comprises the steps of (1) providing a heterogeneous reaction medium consisting of a water-immiscible organic phase and an acidic aqueous phase, wherein the organic phase comprises a mixture of a R—CHO aldehyde compound and a halopyrazine compound corresponding to the formula:

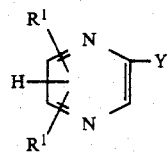

where Y is a halogen atom, and $R^1$ is a substituent selected from hydrogen and alkyl groups containing between about 1-6 carbon atoms, and R in the aldehyde compound is a substituent selected from aliphatic, alicyclic and aromatic groups containing between about 2-12 carbon atoms; (2) maintaining efficient contact between the organic and aqueous phases for a period of time sufficient to achieve acylation of the halopyrazine compound in the presence of a free radical generating agent; and (3) recovering a halo-acylpyrazine product corresponding to the formula:

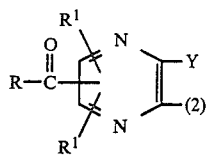

where Y, R and $R^1$ are as previously defined, with the proviso that the position-(2) substituent is not hydrogen.

The halo-acylpyrazine product can be recovered by conventional methods such as extraction of the reaction product medium with an organic solvent (e.g., methylene chloride) as illustrated in Example I. The halopyrazine starting materials can be prepared by suitable halogenation of the pyrazine structure. J. Agric. Food Chem., 23(4), 638(1975) describes the halogenation of alkylsubstituted pyrazine compounds with chlorine or sulfuryl chloride.

General procedures for the preparation of halopyrazines are described in publications such as J. Am. Chem. Soc., 74, 1580(1952); J. Agric. Food Chem., 20, 682(1972); J. Org. Chem., 26, 2356(1961); J. Chem. Soc., Perkin I, 2004(1972); and J. Org. Chem., 26, 2360(1961).

Preparation of Tobacco Compositions

The present invention smoking compositions can be prepared by admixing natural tobacco and/or reconstituted tobacco and/or a non-tobacco substitute with between about 0.00001 and 2 weight percent, and preferably 0.0001–2 weight percent, based on the weight of the smoking composition, of a flavorant additive which corresponds to one of the structural formula set forth hereinabove in definition of the acylpyrazine ether compounds.

An invention acylpyrazine ether flavorant additive can be incorporated into the tobacco in accordance with methods known and used in the art. Preferably the flavorant additive is dissolved in a solvent such as water, alcohol, or mixtures thereof, and then sprayed or injected into the tobacco or non-tobacco substitute matrix. Such method ensures an even distribution of the flavorant additive throughout the tobacco, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or non-tobacco substitute filler in a concentration between about 0.5–5 weight percent, based on the weight of filler, and then subsequently to blend the treated filler with filler which does not contain flavorant additive.

The term "non-tobacco substitute" is meant to include smoking filler materials such as are disclosed in U.S. Pat. Nos. 3,529,602; 3,703,177; 3,796,222; 4,019,521; 4,079,742; and references cited therein; incorporated herein by reference.

Illustratively, U.S. Pat. No. 3,529,602 describes a burnable sheet which may be used as a tobacco substitute, which sheet contains ingredients which include (1) a film-forming ingredient comprising a pectinaceous material derived from tobacco plant parts and having an acid value in excess of 30 milligrams of potassium hydroxide per gram, and (2) a mineral ingredient comprising an alkali metal salt, an alkaline earth metal salt or clay.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or other carbohydrate material at a temperature of 150°–750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

When a present invention acylpyrazine ether is incorporated into smoking material as a flavorant additive, and cigarettes are manufactured from the flavored blend, under smoking conditions the cigarettes have a fuller flavor amplitude and/or other desirable properties in comparison with control cigarettes which do not contain an invention acylpyrazine ether flavorant additive, as demonstrated in Example VIII.

The following examples are further illustrative of the present invention. The reactants and other specific ingredients are presented as being typical, and various modifications can be derived in view of the foregoing disclosure within the scope of the invention.

EXAMPLE I

Preparation Of 1-(3-Chloro-2-pyrazinyl)-1-propanone

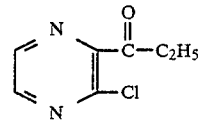

To a stirring heterogeneous mixture of 2-chloropyrazine (1.14 g, 10 mmoles) and freshly distilled propionaldehyde (3.48 g, 60 mmoles) in 5.5 ml of 5.2 M sulfuric acid, at 3° C., is added concurrently 70% t-butyl hydroperoxide (5.4 g, mmoles) 42 and a solution of ferrous sulfate (16.7 g, 60 mmoles) in 40 ml of water over a 5 minute period. The resulting heterogeneous mixture is stirred an additional 1 hour during which time the temperature is raised to 15° C. Solid sodium sulfite is then added until test with starch-iodide paper is negative.

The aqueous mixture is extracted with methylene chloride (3×100 ml), and the extracts are combined and washed with water. After drying (MgSO4), the solvent is removed under reduced pressure to give 1.5 g of a crude product mixture.

The product mixture is passed thru a silica gel column in 15% acetone/hexane, followed by preparative thick layer chromatography (2000μ silica gel GF, developed with 10% acetone/hexane) to provide a 15% yield of 1-(3-chloro-2-pyrazinyl)-1-propanone.

An analytically pure sample is obtained by preparative GLC, and IR and NMR spectra confirm the structure.

EXAMPLE II

Preparation of 1-(3-Ethylthio-2-pyrazinyl)-1-propanone

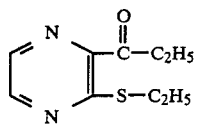

A mixture of sodium ethoxide (100 mg, 1.47 mmoles) and ethanethiol (110 mg, 1.77 mmoles) in 7 ml of absolute ethanol is stirred under nitrogen at room temperature for 10 minutes. 1-(3-Chloro-2-pyrazinyl)-1-propanone (250 mg, 1.47 mmoles) in 5 ml absolute ethanol is added to the above mixture, and the reaction mixture is stirred for 4 hours at which time thin layer chromatography indicates that all of the starting materials have reacted. The mixture is poured into water (100 ml) and extracted with methylene chloride (3×10 ml), and the extracts are combined and washed with water (1×50 ml) and saturated NaCl solution (1×50 ml). After drying (MgSO₄), the solvent is removed under reduced pressure to give an 87% yield of 1-(3-ethylthio-2-pyrazinyl)-1-propanone (m.p. 45°-48° C.).

An analytically pure sample is obtained by preparative GLC, and IR, NMR and MS spectra confirm the structure.

Anal. calc. for $C_9H_{12}N_2OS$: C,55.08; H,6.18; N,14.09; S,16.47.

Found: C,54.91; H,6.16; N,14.27; S,16.34.

EXAMPLE III

Preparation Of
1-(3-Chloro-2-pyrazinyl)-2-methyl-1-propanone

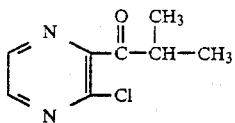

To a stirring mixture of 2-chloropyrazine (5.0 g, 43.6 mmoles), freshly distilled isobutyraldehyde (15.8 g, 218 mmoles), 65.5 ml of glacial acetic acid, 13.1 ml of concentrated sulfuric acid, and 65 ml of water, at about 5° C., is added ferrous sulfate (24.3 g, 87.4 mmoles) in 45 ml of water over a 10 minute period, followed by rapid treatment with 70% t-butyl hydroperoxide (11.2 g, 87 mmoles). The reaction mixture is brought to room temperature and stirred for 1.5 hours. Solid sodium sulfite is added until test with starch-iodide paper is negative. After extracting with benzene (3×100 ml), the combined extracts are washed with saturated sodium bicarbonate solution (75 ml) and saturated brine (75 ml), and then dried (MgSO₄).

Following concentration, the resultant crude product is subjected to distillation (70°-145° C. at 0.2-0.1 mmHg) followed by column chromatography (silica gel 60, eluted with 3% acetone/hexane) to provide a 20% yield of 1-(3-chloro-2-pyrazinyl)-2-methyl-1-propanone.

An analytically pure sample is obtained by preparative GLC, and IR, NMR and MS spectra confirm the structure.

Anal. calc. for $C_8H_9N_2OCl$: C,52.04; H,4.91; N,15.17; Cl19.20.

Found: C,51.92; H,4.94; N,15.06; Cl19.30.

EXAMPLE IV

Preparation Of
1-(3-Methoxy-2-pyrazinyl)-2-methyl-1-propanone

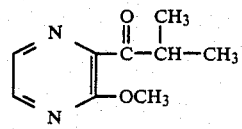

To a stirring solution of 1-(3-chloro-2-pyrazinyl)-2-methyl-1-propanone (513 mg, 2.78 mmoles) under nitrogen at about 5° C. is added 8.8 ml 0.35 M sodium methoxide solution (165 mg, 3.06 mmoles). The bright yellow solution is stirred at room temperature for 1 hour and then refluxed for 1.5 hours, and GLC analysis indicates a complete reaction.

The mixture is diluted with 75 ml of water, followed by extracting with diethyl ether (3×75 ml) and washing of the combined ethereal layers with water (50 ml) and saturated brine (50 ml). After drying (MgSO₄), the solvent is removed under reduced pressure to provide a quantitative yield of 1-(3-methoxy-2-pyrazinyl)-2-methyl-1-propanone.

An analytically pure sample is obtained by preparative GLC, and IR, NMR and MS spectra confirm the above structure.

Anal. calc. for $C_9H_{12}N_2O_2$: C,59.99; H,6.71; N,15.54.

Found: C,59.93; H,6.88, N,15.78.

The structure of the product compound (i.e., the 2,3-disubstitution) is proved by reacting the compound with NaBH₄ to give an alcohol which is found to be identical to that obtained by oxidizing the known 2-methoxy-3-isobutylpyrazine.

EXAMPLE V

Preparation Of
1-(3-Furfurylthio-2-pyrazinyl)-2-methyl-1-propanone

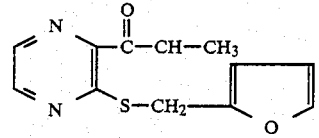

A mixture of sodium ethoxide (148 mg, 2.18 mmoles) and furfuryl mercaptan (285 mg, 2.50 mmoles) in 8 ml of absolute ethanol is stirred under nitrogen at room temperature for 20 minutes. 1-(3-Chloro-2-pyrazinyl)-2-methyl-1-propanone (400 mg, 2.17 mmoles) in 4 ml of absolute ethanol is then added to the reaction medium, and the reaction medium is stirred for 2 hours. Thin layer chromatography (silica gel GF, 20% acetone/hexane) indicates complete reaction, and the mixture is then poured into 100 ml of water. After extracting with methylene chloride (3×100 ml), the combined extracts are washed with saturated sodium bicarbonate (50 ml)

and with saturated sodium chloride (50 ml). After drying (MgSO$_4$), the solvent is removed under reduced pressure to give 450 mg of crude product.

Column chromatography (silica gel 60, eluted with 10% acetone/hexane) followed by crystallization from hexane provides a 32% yield of 1-(3-furfurylthio-2-pyrazinyl)-2-methyl-1-propanone as yellow needles (m.p. 57°–58° C.). The structure of the product compound is confirmed by IR, NMR and MS spectra.

Anal. calc. for C$_{13}$H$_{14}$N$_2$O$_2$S: C,59.52; H,5.38; N,10.68; S,12.22.

Found: C,59.77; H,5.40; N,10.79; S,12.37.

EXAMPLE VI

Preparation Of
1-(5-Chloro-3,6-dimethyl-2-pyrazinyl)-1-propanone

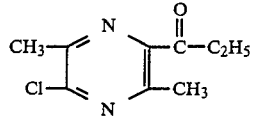

The reaction of 2-chloro-3,6-dimethylpyrazine and propionaldehyde is conducted on a 0.05 mole scale as described in Example III, with the exception that hexane is used as the extracting solvent.

Short path distillation (60° C. at 0.1 mm Hg) affords a 68% yield of 1-(5-chloro-3,6-dimethyl-2-pyrazinyl)-1-propanone.

An analytically pure sample is obtained by preparative GLC, and IR, NMR and MS data confirm the structure.

Anal. Calc. for C$_9$H$_{11}$N$_2$OCl: C,54.42; H,5.58; N,14.10; Cl,17.85.

Found: C,54.54; H,5.57; N,14.23; Cl,18.04.

EXAMPLE VII

Preparation Of
1-[3,6-Dimethyl-5-(cis-hex-3-enoxy)-2-pyrazinyl]-1-propanone

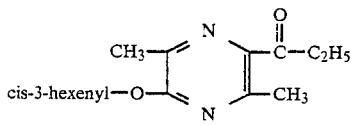

cis-3-hexenol (4 ml) is slowly added to solid sodium hydride (114 mg, 4.75 mmoles) under nitrogen at ~5° C. After the addition is completed and the gas evolution has subsided, the mixture is stirred for 30 minutes at 5°–10° C. 1-(5-Chloro-3,6-dimethyl-2-pyrazinyl)-1-propanone (750 mg, 3.78 mmoles) in 1 ml of cis-3-hexenol is added and the reaction mixture is stirred for 3 hours at room temperature. The resultant product mixture is quenched with water and extracted with diethyl ether (3×25 ml), and the combined extracts are washed with water (20 ml).

After drying (MgSO$_4$), the solvent is removed under reduced pressure and excess cis-3-hexenol is removed by bulb-to-bulb distillation (oven temp. 50° C. at 0.05 mmHg). A quantitative yield of 1-(3,6-dimethyl-5-(cis-hex-3-enoxy)-2-pyrazinyl)-1-propanone is obtained.

An analytically pure sample is obtained by preparative GLC, and IR, NMR and MS spectra confirm the structure.

Anal. calc. for C$_{15}$H$_{22}$N$_2$O$_2$: C,68.67; H,8.45; N,10.68.
Found: C,68.74; H,8.23; N,10.66.

EXAMPLE VIII

Preparation of Present Invention Smoking Compositions Containing a Novel Acylpyrazine Ether Flavorant Cigarettes fabricated to deliver 8 mg of tar using a typical blend of tobaccos are treated with an ethanolic solution of an acylpyrazine ether flavorant as listed in the Table, with the indicated ppm of the compound by weight of the tobacco. Untreated control cigarettes are prepared using the identical tobacco blend and spiked with unflavored ethanol, and the treated cigarettes are compared to the controls by an experienced smoking panel.

Each subjective evaluation involves a set of three cigarettes, two of which are unflavored control cigarettes, and the third is one treated with a flavorant.

The flavorant-treated cigarettes are found to have the smoke flavor properties described in the Table, as compared to the controls.

TABLE

| EXAMPLE | COMPOUND | PPM | ODOR | SMOKE FLAVOR PROPERTIES |
|---|---|---|---|---|
| II | (structure) | 314 | Sharp, caramel, roasted, musty, earthy, cabbage | Smoother, light sweet apple note, slight burnt phenolic |
| IV | (structure) | 370 | Green, sharp, vegetable, isovaleric acid character | Green-sour, fuller |

| EXAMPLE | COMPOUND | PPM | ODOR | SMOKE FLAVOR PROPERTIES |
|---------|----------|-----|------|-------------------------|
| V | 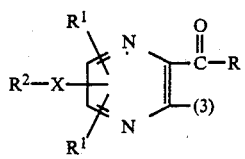 | 400 | No aroma at room temperature, roasted meat when heated | Fuller, dry-roasted peanut husk, smoother |
| VII | 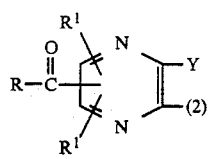 | 360 | Sweet, green, roasted, caramel | Green caramel note |

What is claimed is:

1. An acylpyrazine ether corresponding to the formula:

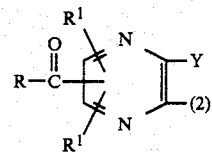

where R is a substituent selected from aliphatic, alicyclic and aromatic hydrocarbyl groups having 2–12 carbon atoms, $R^1$ is a substituent selected from hydrogen and alkyl groups having 1–6 carbon atoms, X is etheric oxygen or sulfur, and $R^2$ is a substituent selected from aliphatic, alicyclic and aromatic hydrocarbyl groups having 1–12 carbon atoms, with the proviso that the position-(3) substituent is not hydrogen.

2. 1-(3-Ethylthio-2-pyrazinyl)-1-propanone.
3. 1-(3-Methoxy-2-pyrazinyl)-2-methyl-1-propanone.
4. 1-(3-Furfurylthio-2-pyrazinyl)-2-methyl-1-propanone.
5. 1-[3,6-Dimethyl-5-(cis-hex-3-enoxy)-2-pyrazinyl]-1-propanone.
6. A halo-acylpyrazine corresponding to the formula:

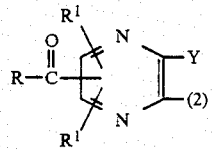

where Y is a halogen atom, R is a substituent selected from aliphatic, alicyclic and aromatic hydrocarbyl groups having 2–12 carbon atoms, and $R^1$ is a substituent selected from hydrogen and alkyl groups having 1–6 carbon atoms, with the proviso that the position-(2) substituent is not hydrogen.

7. 1-(3-Chloro-2-pyrazinyl)-1-propanone.
8. 1-(3-Chloro-2-pyrazinyl)-2-methyl-1-propanone.
9. 1-(5-Chloro-3,6-dimethyl-2-pyrazinyl)-1-propanone.

10. A halo-acylpyrazine corresponding to the formula:

where Y is a chlorine atom, R is a substituent selected from aliphatic, alicylclic and aromatic hydrocarbyl groups having 2–12 carbon atoms, and $R^1$ is a substituent selected from hydrogen and alkyl groups having 1–6 carbon atoms, with the proviso that the position-(2) substituent is not hydrogen.

11. A halo-acylpyrazine corresponding to the formula:

where Y is a bromine atom, R is a substituent selected from aliphatic, alicylclic and aromatic hydrocarbyl groups having 2–12 carbon atoms, and $R^1$ is a substituent selected from hydrogen and alkyl groups having 1–6 carbon atoms, with the proviso that the position-(2) substituent is not hydrogen.

* * * * *